US00PP34384P3

(12) United States Plant Patent
Schoone

(10) Patent No.: US PP34,384 P3
(45) Date of Patent: Jun. 28, 2022

(54) ***PHALAENOPSIS* PLANT NAMED 'FORBIDDEN FRUIT'**

(50) Latin Name: *Phalaenopsis hybrida*
Varietal Denomination: Forbidden Fruit

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 39 days.

(21) Appl. No.: 17/339,964

(22) Filed: Jun. 5, 2021

(65) Prior Publication Data

US 2021/0385990 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'Forbidden Fruit', QZ PBR 2020/2185, filed Sep. 17, 2020.*
CPVO hit on *Phalaenopsis* plant named, 'Forbidden Fruit', application No. 20202185, filed Sep. 17, 2020, downloaded from https://online.plantvarieties.eu/publicConsultationDetails?registerId=20202185&denomination=forbidden&denominationFilter=contains.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'Forbidden Fruit', characterized by its upright plant habit; vigorous growth habit; strong flowering stems; strong leaves; freely flowering habit with typically two inflorescences per plant, each inflorescence with numerous flowers; large pale yellow-colored flowers with reddish purple-colored stripes and venation and blushed with pastel pink; and good postproduction longevity.

2 Drawing Sheets

Figure 1:
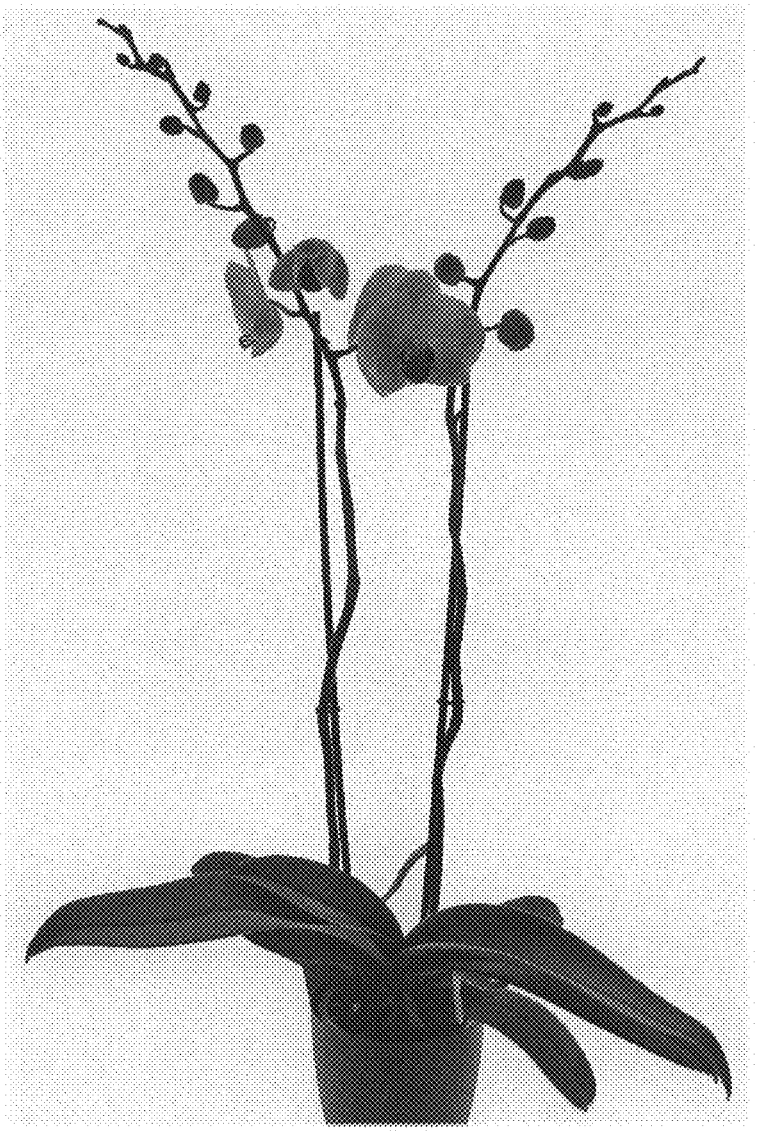

Botanical designation: *Phalaenopsis hybrida.*
Cultivar denomination: 'FORBIDDEN FRUIT'.

CROSS-REFERENCED TO CLOSELY-RELATED APPLICATIONS

Title: Varieties of *Phalaenopsis* Plants
Inventor: René Schoone
Filed: Jun. 6, 2020
Ser. No. 62/705,003
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2185. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Forbidden Fruit'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in June, 2014 in De Lier, The Netherlands of *Phalaenopsis hybrida* 'Magic Art', not patented, as the female, or seed, parent with a proprietary selection of *Phalaenopsis hybrida* identified as code number WM 559, not patented, as the male, or pollen, parent. The new

*Phalaenopsis* plant was discovered and selected by the Inventor as a single flowering plant from within the progeny of the stated cross-pollination grown in a controlled greenhouse environment in Heemskerk, The Netherlands in March, 2017.

Asexual reproduction of the new *Phalaenopsis* plant by in vitro meristem propagation in a controlled environment in Assendelft, The Netherlands since March, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Forbidden Fruit'. These characteristics in combination distinguish 'Forbidden Fruit' as a new and distinct *Phalaenopsis* plant:

1. Upright plant habit.
2. Vigorous growth habit.
3. Strong flowering stems.
4. Strong leaves.
5. Freely flowering habit with typically two inflorescences per plant, each inflorescence with numerous flowers.
6. Large pale yellow-colored flowers with reddish purple-colored stripes and venation and blushed with pastel pink.
7. Good postproduction longevity.

Plants of the new *Phalaenopsis* can be compared to plants of the female parent, 'Magic Art'. Plants of the new *Phalaenopsis* differ primarily from plants of 'Magic Art' in flower color as flowers of plants of the new *Phalaenopsis* are pale yellow in color with reddish purple-colored stripes and venation and blushed with pastel pink whereas flowers of plants of 'Magic Art' are white in color blushed with violet with purple and pink-colored dots and stripes.

Plants of the new *Phalaenopsis* can be compared to plants of the male parent selection. Plants of the new *Phalaenopsis* differ primarily from plants of the male parent selection in flower color as flowers of plants of the new *Phalaenopsis* are pale yellow in color with reddish purple-colored stripes and venation and blushed with pastel pink whereas flowers of plants of the male parent selection are white in color blushed with violet without stripes or distinct venation.

Plants of the new *Phalaenopsis* can be compared to plants of *Phalaenopsis hybrida* 'Caribbean Dream', not patented. In side-by-side comparisons, plants of the new *Phalaenopsis* differ primarily from plants of 'Caribbean Dream' in flower color as flowers of plants of the new *Phalaenopsis* pale yellow in color with reddish purple-colored stripes and venation and blushed with pastel pink whereas flowers of 'Caribbean Dream' are pale yellow in color blushed with orange. In addition, plants of the new *Phalaenopsis* are taller than plants of 'Caribbean Dream'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Forbidden Fruit' grown in a container.

Figure 2:
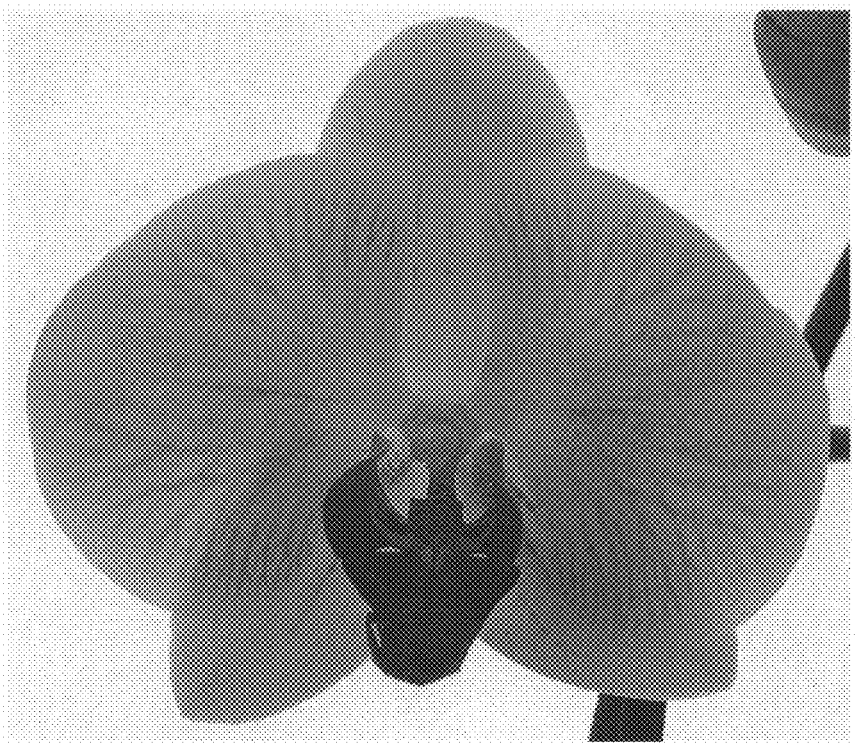

The photograph on the second sheet (FIG. 2) is a close-up view of a typical flower of 'Forbidden Fruit'.

DETAILED BOTANICAL DESCRIPTION

The aforementioned photographs and following observations and measurements describe plants grown during the early winter in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Forbidden Fruit'.

Parentage:

*Female parent.*—*Phalaenopsis hybrida* 'Magic Art', not patented.

*Male parent.*—Proprietary selection of *Phalaenopsis hybrida* identified as code number WM 559, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two inflorescences per plant, each inflorescence with numerous flowers; monopodial; vigorous growth habit and rapid growth rate.

*Plant height, substrate level to top of foliar plane.*—About 15.6 cm.

*Plant height, substrate level to top of inflorescences.*—About 60.4 cm.

*Plant diameter or spread.*—About 36 cm.

Leaf description:

*Arrangement and quantity.*—Distichous, simple; sessile; about eight leaves per plant.

*Length.*—About 25.2 cm.

*Width.*—About 7.4 cm.

*Aspect*.—Upright to outwardly arching.

*Shape*.—Oblanceolate to oblong; slightly carinate.

*Apex*.—Unequal acute to unequal broadly acute.

*Base*.—Sheathing. Sheath length: About 2.2 cm. Sheath width: About 1.7 cm. Sheath color: Close to 143C; towards the distal margin, close to 143A to 143B.

*Margin*.—Entire; slightly revolute.

*Texture and luster, upper and lower surfaces*.—Smooth, glabrous; slightly glossy.

*Venation pattern*.—Camptodromous.

*Color*.—Developing leaves, upper surface: Slightly darker than between 146A and 147A. Developing leaves, lower surface: Close to 147B strongly tinged with close to N77A. Fully expanded leaves, upper surface: Close to between 137B and 146A; venation, close to NN137B. Fully expanded leaves, lower surface: Close to 146B slightly tinged with close to between N77A and 200B; venation, close to 144A tinged with close to N77A.

Inflorescence description:

*Appearance and flowering habit*.—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 28.8 cm.

*Inflorescence width*.—About 16.3 cm.

*Flower buds*.—Height: About 2 cm. Diameter: About 1.5 cm by 1.6 cm. Shape: Broadly ovate. Color: Close to 144A; upper surface, moderately tinged with close to 177A to 177B.

*Flower size*.—Large, about 8.5 cm (vertical) by 9.4 cm (horizontal).

*Flower depth*.—About 3.5 cm.

*Petals, quantity and arrangement*.—Three, two lateral petals and one center petal transformed into a labellum.

*Lateral petals*.—Length: About 4.9 cm. Width: About 6.1 cm. Shape: Reniform to lunate. Apex: Obtuse. Margin: Entire. Texture and luster, upper and lower surfaces: Smooth, glabrous, velvety; matte. Color: When opening, upper surface: Close to 1C to 1D; towards the base, close to 2D to lighter than 2D, and at the base (at column connection), close to 75A; center, slightly tinged with close to 60C; venation, close to 60C. When opening, lower surface: Close to between 1C and 2C; venation visible from upper surface, close to 182B and 182C. Fully opened, upper surface: Close to between 11D and 157D; at the base (at column connection), close to N75C; center, slightly tinged with close to 70B; venation, close to 70B. Fully opened, lower surface: Close to between 11D and 157C; venation visible from upper surface, close to 185D.

*Labella*.—Appearance: Three-parted with two lateral lobes and a central lobe. Length, lateral lobes: About 2.2 cm. Width, lateral lobes: About 1.5 cm. Length, central lobe: About 3.9 cm. Width, central lobe: About 9 mm to 22 mm. Shape, lateral lobes: Obovate. Shape, central lobe: Deltoid. Apex, lateral lobes: Obtuse. Apex, central lobe: Cleft with two narrow and strongly recurved cirrose tips, about 1.8 cm in length and about 1.3 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 4 mm in length, about 6 mm in width and about 5 mm in height. Color: When opening, upper surface: Lateral lobes: Close to 59B; distally, close to 70A; axillary stripes, close to 76C. Central lobe: Close to 59C to 59D; distally, tinged with close to 178C; at the base (at column connection) close to 157D; radial stripes, close to 183C; cirrose tips, close to 59D. Callosities: Close to 13A; fine dots, close to 183C. When opening, lower surface: Lateral lobes: Close to 59B; distally, close to N78C to N78D; at the base, close to 156B. Central lobe: Close to 156C to 156D; distally, close to 157D to lighter than 157D; towards the margins, close to 59C, 60C and 72B; at the base (at column connection) close to 156C to 156D; cirrose tips, close to 59D. Fully opened, upper surface: Lateral lobes: Close to 59B; distally, close to 70A; axillary stripes, close to 76C. Central lobe: Close to 59C to 59D; distally, tinged with close to 178C; at the base (at column connection) close to NN155B; radial stripes, close to 183C; cirrose tips, close to 59D. Callosities: Close to 13A; fine dots, close to 183C. Fully opened, lower surface: Lateral lobes: Close to 59B; distally, close to N78C to N78D; at the base, close to 156B. Central lobe: Close to 156C to 156D; distally, close to 157D to lighter than 157D; towards the margins, close to 59C, 60C and 72B; at the base (at column connection) close to 156C to 156D; cirrose tips, close to 59D.

*Sepals*.—Quantity and arrangement: Three, one upper dorsal sepal and two lower lateral sepals. Length, dorsal sepal: About 4.9 cm. Width, dorsal sepal: About 3.5 cm. Length, lateral sepals: About 5 cm. Width, lateral sepals: About 3.2 cm. Shape, dorsal sepal: Broadly elliptic to oblong. Shape, lateral sepals: Ovate. Apex, dorsal sepal: Obtuse. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to 1C and 2C; venation, close to 184D. When opening, lower surface: Close to 151D; distally, tinged with close to 185D; towards the margins and apex, close to 154D. Fully opened, upper surface: Close to 150D; towards the margins, apex and base, close to between 155A and 147D; venation, close to 64B. Fully opened, lower surface: Close to 150D; distally, tinged with close to 185D;

towards the margins and apex, close to 4D. Color, lateral sepals: When opening, upper surface: Close to between 2C and 154D; towards the base, close to 154C and at the base, blotched and dotted, close to 174B; venation, close to 185B. When opening, lower surface: Close to between 144C and N144B; towards the margins and apex, slightly tinged with close to 177D to lighter than 177D; main vein, close to 144B. Fully opened, upper surface: Lighter than between 4D and 157B; towards the base, close to 1C to 1D and at the base, blotched and dotted, close to 174B to 174C; venation, close to 185B. Fully opened, lower surface: Close to 2C to 2D; towards the margins and apex, slightly tinged with lighter than 185D.

*Peduncles*.—Length: About 39.6 cm. Diameter: About 6 mm. Strength: Strong. Aspect: Upright to outwardly arching. Texture and luster: Smooth, glabrous; matte. Color: Close to 146A to 146B, densely covered with fine dots, close to between N186C and 200A.

*Pedicels*.—Length: About 4 cm. Diameter: About 4 mm. Strength: Moderately strong. Aspect: About 80° from peduncle axis. Texture and luster: Smooth, glabrous; matte. Color: Close to 144C; distally, close to 154D and proximally, close to between 146A and 148A.

*Reproductive organs*.—Androecium: Column length: About 8 mm. Column width: About 7 mm. Column color: Close to NN155B. Pollinia quantity: Two. Pollinia diameter (per two pollinia): About 2.25 mm. Pollinia color: Close to 25B. Gynoecium: Stigma length: About 4 mm. Stigma width: About 6 mm. Stigma shape: Reniform. Stigma color: Close to 157B. Ovary length: About 7 mm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Forbidden Fruit' as illustrated and described.

* * * * *